United States Patent [19]

Inouye et al.

[11] 4,017,607

[45] Apr. 12, 1977

[54] 9,3'',4''-TRIACYL ESTER OF THE ANTIBIOTIC SF-837 $M_1$ SUBSTANCE AND THE PRODUCTION THEREOF

[75] Inventors: Shigeharo Inouye, Yokohama; Shoji Omoto, Tokyo; Katsuyoshi Iwamatsu, Ayase; Takashi Tsuruoka, Kawasaki; Taro Niida, Yokohama; Toyoaki Kawasaki, Tokyo, all of Japan

[73] Assignee: Meiji Seika Kaisha, Ltd., Tokyo, Japan

[22] Filed: July 18, 1975

[21] Appl. No.: 597,188

Related U.S. Application Data

[63] Continuation-in-part of Ser. No. 475,311, May 31, 1974, abandoned.

[30] Foreign Application Priority Data

Aug. 27, 1974 Japan .............................. 49-97485

[52] U.S. Cl. .................................. 424/180; 536/9; 536/17
[51] Int. Cl.$^2$ ....................................... C07H 17/08
[58] Field of Search ................ 260/210 AB; 536/17

[56] References Cited

UNITED STATES PATENTS

| | | | |
|---|---|---|---|
| 3,792,035 | 2/1974 | Fukatsu et al. | 260/210 AB |
| 3,853,842 | 12/1974 | Kishi et al. | 260/210 AB |
| 3,855,202 | 12/1974 | Omoto et al. | 260/210 AB |

*Primary Examiner*—Johnnie R. Brown
*Attorney, Agent, or Firm*—Larson, Taylor and Hinds

[57] ABSTRACT

As new compounds are provided 9,3'',4''-trialkanoyl SF-837 $M_1$ substances which have therapeutically useful antibacterial activity and do not show any objectionable long-lasting bitter taste upon its oral administration. These 9,3'',4''-trialkanoyl SF-837 $M_1$ substances may be prepared from SF-837 substance, 9,2',3''-tri-acetyl SF-837 $M_1$ substance, 9,2'-di-acetyl SF-837 substance, 9-propionyl SF-837 substance or 9,2'-dipropionyl SF-837 substance by acylating the latter with an alkanoic acid anhydride at 50°–120° C to produce the corresponding 9,2',3'',4''-tetra-alkanoyl SF-837 $M_1$ substance and occasionally the 9,18,2',3'',4''-penta-alkanoyl SF-837 $M_1$ substance, with involving the shift of the 4''-alkanoyl group to the 3''-hydroxyl group. Partial and selective hydrolysis of the 9,2',3'',4''-tetra-alkanoyl SF-837 $M_1$substance and/or the 9,18,2',3'',4''-penta-alkanoyl SF-837 $M_1$ substance so produced gives the desired 9,3'',4''-tri-alkanoyl SF-837 $M_1$ substance.

8 Claims, No Drawings

9,3'',4''-TRIACYL ESTER OF THE ANTIBIOTIC SF-837 M₁ SUBSTANCE AND THE PRODUCTION THEREOF

The present invention is a continuation-in-part of the earlier filed patent application Ser. No. 475,311, filed on May 31, 1974, now abandoned.

This invention relates to a 9,3'',4''-triacyl ester of SF-837 M₁ substance and more particularly a 9,3'',4''-tri-alkanoyl SF-837 M₁ substance which is a new and useful compound. This invention further rleates to a process for the production of such a 9,3'',4''-tri-alkanoyl SF-837 M₁ substance. The 9,3'',4''-tri-alkanoyl SF-837 M₁ substance according to this invention is a new compound which is useful in a therapeutic treatment of infections by gram-negative and gram-positive bacteria and which is advantageously free from the unpleasant bitter taste of the parent antibiotic SF-837 substance.

The antibotic SF-837 substance is a known useful macrolide antibotic (see, eg. U.S. Pat. No. 3,761,588 and the "Journal of Antibiotic" Vol. 24, No. 7 pages 460–475 (July, 1971) and is such a compund which contains three hydroxyl groups at the 9-, 2'- and 3''-position of the molecule and is represented by the formula (I):

exhibit unpleasant long-lasting bitter taste upon oral administration and are therefore not suitable to be formulated into a liquid preparation which is intended to be given orally to infants who are often not able to swallow the tablet or capsule preparation or to such a person who dislikes the bitter taste of medicament.

An object of this invention is to provide such a new acyl derivative ester of SF-837 substance which is substantially free from the unpleasant bitter taste of the original SF-837 substance as well as the 9,2'-di-acetyl SF-837 substance and the 9-mono-acyl SF-837 substance and which exhibits an antibacterial activity higher than or substantially as high as the parent SF-837 substance. A particular object of this invention is to provide such a new 9,3'',4''-tri-alkanoyl SF-837 M₁ substance which has the above-mentioned therapeutically and pharmaceutically favorable properties. The other object of this invention is to provide a process for the production of the 9,3'',4''-tri-alkanoyl SF-837 M₁ substance from the SF-837 substance or its derivtives. Another objects of this invention will be clear from the descriptions.

We have studied the reactivity of the three hydroxyl groups that is, the 9-, 2'- and 3''- hydroxyl group of SF-837 substance and the 4''-hydroxyl group of SF-837 M₁ substance for their acylation. As a result, we have now found that the 9- and 2'-hydroxyl groups of SF-

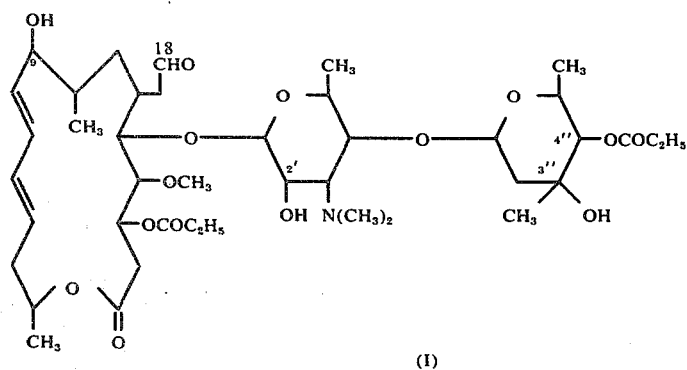

(I)

The Sf-837 M₁ substance is known as a metabolic product which is produced by giving orally the SF-837 substance in rats and is isolated from the urine of rats or a digested solution of the SF-837 subtance with a liver homogenate. SF-837 M₁ substance is a powder product of a melting point of 123°–125° C and $[\alpha]_D^{22} -56°$ ($c$ 1, ethanol). The SF-837 M₁ substance is identified as 4''-depropionyl SF-837 substance (see the "Chemical and Pharmaceutical Bulletin" Vol. 20, No. 11, pages 2366–2371 (1972) and the "Journal of Antibiotic" Vol. 24, No. 8 pages 535 (1971) and contains four hydroxyl groups at the 9-, 2'-, 3''- and 4''- positions of the molecule. The 9-hydroxyl and 2'-hydroxyl groups of the SF-837 substance molecule are relatively reactive while the tertiary 3''-hydroxyl group thereof is less reactive for the acylation (or the esterification) with an alkanoic acid. 9,2'-di-acetyl SF-837 substance is described in the aforesaid U.S. Pat. No. 3,761,588, and 9-mono-acetyl SF-837 substance is described in U.S. Pat. No. 3,792,035. Although the SF-837 substance as well as the 9,2'-di-acetyl SF-837 substance and 9-mono-acetyl SF-837 substance are useful as an agent of treating therapeutically the bacterial infections, these compounds suffer from such a disadvantage that they 837 substance may be acylated by reacting the SF-837 substance with an alkanoic acid anhydride at ambient temperature, and that the 4''-hydroxyl group of the SF-837 M₁ substance may equally be acylated by reacting with an alkanoic acid anhydride at ambient temperature. We have now surprisingly found that when the SF-837 substance or a 4''-alkanoyl SF-837 M₁ substance (that is, the 4''-alkanoyl -4''-depropionyl SF-837 substance) is reacted with an excessive amount of an alkanoic acid anhydride of 2–5 carbon atoms at an elevated temperature of 50° C to 120° C in the presence of an organic base such as pyridine, picoline or triethylamine, the 9- and 2'-hydroxyl groups thereof are acylated with said alkanoic acid anhydride, but the 4''-alkanoyl group of the 4''-alkanoyl SF-837 M₁ substance is shifted to the 3''-hydroxyl group from the 4''-position, while the 4''-position is concomitantly acylated with said alkanoic acid anhydride employed, whereby a 9,2'-4''-tri-alkanoyl-3''-propionyl SF-837 M₁ substance is produced from the SF-837 substance, or a 9,2',3'',4''-tetra-alkanoyl SF837 M₁ substance is produced from the 4''-alkanoyl SF-837 M₁ substance. We have also found that the 9,2',4''-tri-alkanoyl-3''-propionyl SF-837 M₁ substance or the 9,2',3'',4''-tetra-alkanoyl SF-837 M₁ substance so produced can further be acylated by reacting with another amount of the alkanoic acid anhydride at a temperature of 50°–120° C for a prolonged reaction time or at a higher temperature of 110°–120° C, so that even the aldehyde group at the 18-position of the SF-837 substance or SF837 M₁ substance molecule is acylated with said alkanoic acid anhydride to give the corresponding 9,18,2',4''-tetra-alkanoyl-3''-propionyl SF-837 M₁ substance or the corresponding 9,18,2',3'',4''-penta-alkanoyl SF-837 M₁ substance. Moreover, we have discovered that the 9,2',4''-tri-alkanoyl-3''-propionyl SF-837 M₁ substance and the 9,2',3'',4''-tetra-alkanoyl SF-837 M₁ substance may be converted into the corresponding 9,4''-di-alkanoyl-3''-propionyl SF-837 M₁ substance and the corresponding 9,3'',4''-tri-alkanoyl SF-837 M₁ substance, respectively, by subjecting to a partial and selective hydrolysis in an aqueous acetone or in an aqueous alkanol such as a lower alkanol of 1–4 carbon atoms, for example, methanol, ethanol, propanol or butanol containing a proportion of water therein to effect preferential removal of the 2'-alkanoyl group. The 9,18,2',4''-tetra-alkanoyl-3''-propionyl SF-837 M₁ substance and the 9,18,2',3'',4''-penta-alkanoyl SF-837 M₁ substance may equally be converted into the corresponding 9,4''-di-alkanoyl-3''-propionyl SF-837 M₁ substance and the corresponding 9,3'',4''-tri-alkanoyl SF-837 M₁ substance, respectively, by subjecting to a partial and selective hydrolysis in the same manner as mentioned above, to effect preferential removal of the 2'- and 18-alkanoyl groups therefrom.

In this way, we have succeeded in synthethizing as the new acyl derivatives (esters) of the SF-837 substance, 9,4''-di-acetyl-3''-propionyl SF-837 M₁ substance; 9,3''-di-acetyl-4''-propionyl SF-837 M₁ substance; 9-propionyl-4''-acetyl-3''-propionyl SF-837 M₁ substance; 9,3'',4''-tripropionyl SF-837 M₁ substance; 9-acetyl-4''-isobutyl-3''-propionyl SF-837 M₁ substance; 9-acetyl-3'',4''-dipropionyl SF-837 M₁ substance; and 9-acetyl-4''-isovaleryl-3''-propionyl SF-837 M₁ substance. We have found that these new compounds, namely, these 9,3'',4''-tri-alkanoyl SF-837 M₁ substances show practically no bitter taste upon oral administration of them but exhibit improved therapeutic effect in the treatment of the bacterial infections as compared to the original SF-837 substance and have a reduced acute toxicity upon oral administration to mice.

According to a first aspect of this invention, therefore, there is provided as the new compound a 9,3'',4''-tri-alkanoyl SF-837 M₁ substance of the formula (II):

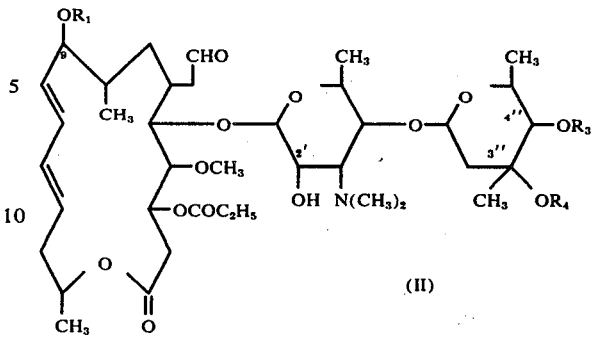

wherein R₁ and R₄ are each acetyl or propionyl group and R₃ is acetyl, propionyl, n-butyryl, isobutyryl or isovaleryl group.

According to a preferred embodiment of this first aspect of the invention, there is provided a 9,3'',4''-tri-alkanoyl SF-837 M₁ substance for the formula (II'):

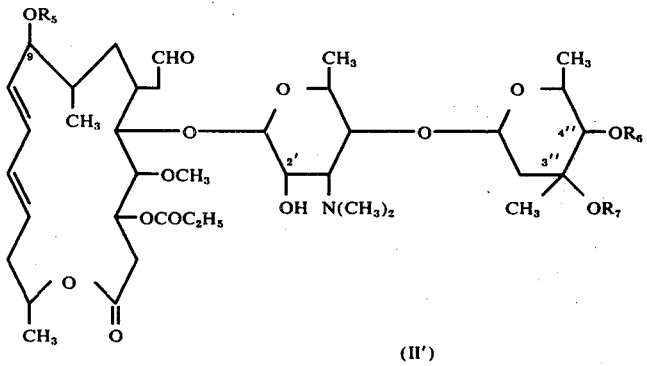

wherein R₅ is acetyl or propionyl group, R₆ is acetyl, propionyl, isobutyryl or isovaleryl group, and R₇ is acetyl or propionyl group, provided when R₅ is acetyl, R₆ is acetyl or propionyl, provided that when R₅ and R₇ are each acetyl, R₆ is propionyl, provided that when R₅ is acetyl and R₇ is propionyl, R₆ is acetyl, propionyl, isobutyryl or isovaleryl, and provided that when R₅ is propionyl, R₆ is acetyl or propionyl and R₇ is propionyl.

Examples of the compound of the formula (II) or (II') are mentioned below.

1. 9,4''-di-acetyl-3''-propionyl SF-837 M₁ substance, being a compound of the formula (II) where R₁ and R₃ are each acetyl and R₄ is propionyl, is a substance which substantially does not show any bitter taste and forms a colorless crystalline product of a melting point of 228°–230° C (with decomposition). [α]_D^{22} −60.0° (c 1%, chloroform). This compound may also be nominated as 9,4''-di-acetyl-3''-propionyl-4''-depropionyl SF-837 substance.

2. 9,3''-di-acetyl-4''-propionyl SF-837 M₁ substance, being a compound of the formula (II) where R₁ and R₄ are each acetyl and R³ is propionyl, is a substance which has practically no bitter taste and forms a colorless crystalline product of a melting point of 198°–203° C (with decomposition). This compound may also be nominated as 9,3''-di-acetyl SF-837 substance.

3. 9-acetyl-4''-isobutyryl-3''-propionyl SF-837 M₁ substance, being a compound of the formula (II) where R₁ is acetyl, R₃ is isobutyryl and R₄ is propionyl, is a substance which substantially does not have any bitter taste and forms a colorless amorphous product of a melting point of 140°–145° C (moistened). This compound may also be termed as 9-acetyl-4''-isobutyryl-4''-depropionyl-3''-propionyl SF-837 substance.

4. 9-acetyl-4''-isovaleryl-3''-propionyl SF-837 $M_1$ substance, being a compound of the formula (II) where $R_1$ is acetyl, $R_3$ is isovaleryl and $R_4$ is propionyl, is a substance which substantially does not have any bitter taste and forms a colorless amorphous product of a melting point of 135°–140° C. This compound may also be nominated as 9-acetyl-4''-isovaleryl-4''-depropionyl-3''-propionyl SF-837 substance.

5. 9,3''-dipropionyl-4''-acetyl SF-837 $M_1$ substance, being a compound of the formula (II) where $R_1$ and $R_4$ are each propionyl and $R_3$ is acetyl, is a substance which substantially does not show any bitter taste and forms a colorless crystalline product of a melting point of 205°–208° C (with decomposition). This compound may also be nominated as 9,3''-dipropionyl-4''-acetyl-4''-depropionyl SF-837 substance.

6. 9-acetyl-3'',4''-dipropionyl SF-837 $M_1$ substance, being a compound of the formula (II) where $R_1$ is acetyl, $R_3$ and $R_4$ are propionyl, is such a substance which substantially does not have the bitter taste and is a colorless crystalline compound of a melting point of 222°–224° C. This compound may also be called as 9-acetyl-3''-propionyl SF-837 substance.

7. 9,3'',4''-tripropionyl SF-837 $M_1$ substance, being a compound of the formula (II) where $R_1$, $R_3$ and $R_4$ are each propionyl, is such a substance which is a colorless amorphous compound of a melting point of 150°–160° C (moistened). When crystallized, it gives a colorless crystalline product of a melting point of 195°–197° C (with slight coloration). This compound may also be called as 9,3''-dipropionyl SF-837 substance.

It has been found that the 9,3'',4''-tri-alkanoyl SF-837 $M_1$ substance of the formula (II) or (II') according to this invention exhibits a high antibacterial activity to gram-negative and gram-positive bacteria as much as the parent SF-837 substance itself and may be utilized as an antibacterial agent in the same manner as the SF-837 substance or the 9,2'-di-acetyl SF-837 substance or the 9-mono-acetyl SF-837 substance for the therapeutic purpose, with the advantage that the new compound of the formula (II) or (II') of this invention may orally be administered in the form of a liquid preparation without giving the objectionable bitter taste. In addition, it has been found that the 9,3'',4''-tri-alkanoyl SF-837 $M_1$ substance of the formula (II) or (II') according th this invention gives a higher curative effect than the original SF-837 substance when it is administered orally to mice which have intrapertioneally been infected with Staphylococcus aureus.

The antibacterial spectra of 9,4''-di-acetyl-3''-propionyl SF-837 $M_1$ substance (abbreviated as Compound No. 1), 9,3''-di-acetyl-4''-propionyl SF-837 $M_1$ substance (abbreviated as Compound No. 2), 9-acetyl-4''-isobutyryl-3''-propionyl SF-837 $M_1$ substance (abbreviated as Compound No. 3), 9-acetyl-4''-isovaleryl-3''-propionyl SF-837 $M_1$ substance (abbreviated as Compound No. 4), 9,3''-dipropionyl-4''-acetyl SF-837 $M_1$ substance (abbreviated as Compound No. 5) 9-acetyl-3'',4''-dipropionyl SF-837 $M_1$ substance (abbreviated as Compound No. 6) and 9,3'',4''-tripropionyl SF-837 $M_1$ substance (abbreviated as Compound No. 7) are shown in Table 1 below, together with the antibacterial spectra of the original SF-837 substance, the 9,2'-di-acetyl SF-837 substance and the 9-mono-acetyl SF-837 substance for the comparison purpose. The minimum inhibitory concentrations (mcg/ml) of these compounds to various test microorganisms were determined according to standard serial dilution method using Brian Heart Infusion broth as the incubation medium, the estimation of the growth of the test organisms being effected after 24 hours' incubation at 37° C.

Table 1

| Microorganism tested | Minimum Inhibitory Concentrations (mcg/ml) | | | | | |
|---|---|---|---|---|---|---|
| | Compound No. 1 | Compound No. 2 | Compound No. 3 | Compound No. 4 | Compound No. 5 | Compound No. 6 |
| Staphylococcus aureus 209P | 1.56 | 1.56 | 1.56 | 1.56 | 1.56 | 1.56 |
| Staphylococcus aureus Terajima | 3.12 | 3.12 | 3.12 | 1.56 | 3.12 | 3.12 |
| Staphylococcus aureus Smith | 0.39 | 0.39 | 0.39 | 1.56 | 0.78 | 0.39 |
| Staphylococcus albus 1200A | 1.56 | 1.56 | 1.56 | 1.56 | 1.56 | 1.56 |
| Streptococcus faecalis ATCC 8043 | 0.78 | 0.78 | 0.78 | 0.78 | 0.78 | 0.78 |
| Streptococcus hemolyticus Cook | 0.19 | 0.19 | 01.9 | 0.39 | 0.39 | 0.19 |
| Streptococcus hemolyticus D-90 | 0.78 | 0.78 | 0.78 | 0.19 | 0.78 | 0.78 |
| Streptococcus pyogenes D-58 | 0.19 | 0.19 | 0.19 | 0.19 | 0.19 | 0.19 |
| Diplococcus pneumoniae Type I | 0.09 | 0.09 | 0.09 | 0.39 | 0.09 | 0.09 |
| Diplococcus pneumoniae Type III | 0.09 | 0.09 | 0.09 | 0.19 | 0.09 | 0.09 |
| Bacillus subtilis PCI 219 | 0.78 | 0.78 | 0.78 | 0.78 | 1.56 | 0.78 |
| Bacillus subtilis ATCC 6633 | 1.56 | 1.56 | 1.56 | 1.56 | 1.56 | 1.56 |
| Bacillus anthracis No. 119 | 0.78 | 0.78 | 1.56 | 1.56 | 0.78 | 0.78 |
| Corynebacterium diphtheriae Type gravis | 0.19 | 0.19 | 0.19 | 0.19 | 0.19 | 0.19 |
| Corynebacterium diphtheriae Type intermedius | 0.19 | 0.19 | 0.19 | 0.19 | 0.19 | 0.19 |
| Sarcina lutea | 0.09 | 0.09 | 0.09 | 0.09 | 0.09 | 0.09 |

| Microorganism tested | Compound No. 7 | SF-837 substance (comparative) | 9,2'-di-acetyl SF-837 substance (comparative) | 9-mono-acetyl SF-837 substance (comparative) |
|---|---|---|---|---|
| Staphylococcus aureus 209P | 0.78 | 0.78 | 1.56 | 1.56 |
| Staphylococcus aureus Terajima | 1.56 | 1.56 | 1.56 | 1.56 |
| Staphylococcus aureus Smith | 0.78 | 0.19 | 0.39 | 0.78 |
| Staphylococcus albus 1200A | 1.56 | 0.78 | 1.56 | 0.78 |
| Streptococcus faecalis ATCC 8043 | 0.78 | 1.56 | 3.12 | 1.56 |
| Streptococcus hemolyticus Cook | 0.19 | 0.09 | 0.19 | 0.39 |
| Streptococcus hemolyticus D-90 | 1.56 | 1.56 | 1.56 | 1.56 |
| Streptococcus pyogenes D-58 | 0.09 | 0.09 | 0.19 | 0.39 |
| Diplococcus pnemoniae Type I | 0.19 | 0.04 | 0.09 | 0.04 |
| Diplococcus pneumoniae Type III | 0.09 | 0.04 | 0.09 | 0.04 |
| Bacillus subtilis PCI 219 | 0.78 | 0.78 | 0.78 | 0.78 |
| Bacillus subtilis ATCC 6633 | 1.56 | 1.56 | 3.12 | 1.56 |

Table 1-continued

| | Minimum Inhibitory Concentrations (mcg/ml) | | | |
|---|---|---|---|---|
| Bacillus anthracis No. 119 | 0.78 | 0.78 | 1.56 | 1.56 |
| Corynebacterium diphtheriae Type gravis | 0.19 | 0.19 | 0.39 | 0.19 |
| Corynebacterium diphtheriae Type intermedius | 0.19 | 0.19 | 0.19 | 0.19 |
| Sarcina lutea | 0.09 | 0.09 | 0.19 | 0.09 |

The curvature effect of the 9,3'',4''-tri-alkanoyl SF-837 $M_1$ substance of the formula (II) or (II') of this invention in a therapeutic treatment of *Staphylococcus aureus* 209P infections in mice was tested in the following way: Thus, an aqueous suspension of a pathogenic *Staphylococcus aureus* 209P in an aqueous solution of 5% gastric mucin was injected intraperitoneally to mice each at an inoculum size of 100 times higher than the $LD_{50}$ quantity of said strain for inoculation. The mice were classified into several groups each consisting of 10 mice. A dosage of 100 mg/kg or 200 mg/kg of a test compound suspended in an aqueous solution of 2% gum arabic was then given orally to the infected mice immediately after the inoculation. The mice so treated were then usually raised for 7 days, and the 7th day after the administration of the test compound, the number of the surviving mice in each group was counted. The test results obtained are shown in Table 2 below.

Table 2

| Test Compound* | Rate of surviving mice in each group of mice | |
|---|---|---|
| | Dosage 100 mg/kg | Dosage 200 mg/kg |
| Compound No. 1 | 6/10 | 10/10 |
| Compound No. 2 | 8/10 | 10/10 |
| Compound No. 3 | 4/10 | 10/10 |
| Compound No. 4 | 0/10 | 3/10 |
| Compound No. 5 | 4/10 | 8/10 |
| Compound No. 6 | 6/10 | 10/10 |
| Compund No. 7 | 5/10 | 10/10 |
| SF-837 substance (comparative) | 0/10 | 6/10 |
| 9,2'-di-acetyl SF-837 substance (comparative) | 0/10 | 6/10 |
| 9-mono-acetyl SF-837 substance (comparative) | 5/10 | 8/10 |

*In Table 2, Compound Nos. 1 to 5 are the same as given in Table 1 mentioned above. As will be clear from the results of the above tables, 9,3''-di-acetyl 4''-propionyl SF-837 $M_1$ substance (Compound No. 2, which may also be termed as 9,3''-di-acetyl SF-837 substance) is most preferred among the compounds of the formula (II) or (II') according to this invention.

When acute toxicity was determined by oral administration to several groups of mice each consisting of 5 mice, it was found that the 9,3'',4''-tri-alkanoyl SF-837 $M_1$ substance of this invention exhibited an $LD_0$ value of more than 3,200 mg/kg, whereas the original SF-837 substance (the free base) exhibited an $LD_{50}$ value of 3,200 mg/kg. In addition, the 9,3'',4''-tri-alkanoyl SF-837 $M_1$ substance of this invention do not or practically not exhibit the bitter taste which is usually inherent to the macrolide antibiotics, so that the new compound of this invention is advantageously suitable to be formulated as a liquid preparation which is intended to be given orally to infants. In view of all the above-mentioned micro-biological and physiological properties of the 9,3'',4''-tri-alkanoyl SF-837 $M_1$ substance of this invention, it will be clear that the 9,3'',4''-tri-alkanoyl SF-837 $M_1$ substance of this invention has the significantly improved properties as the antibacterial agent, as compared to the original SF-837 substance. The 9,3'',4''-tri-alkanoyl SF-837 $M_1$ substance of this invention may be formulated into an aqueous solution or suspension in a conventional pharmaceutical manner for oral administration and also for injection, and they may, of course, be made up into the other various formulations such as tablets, capsules, pulver and granules with aid of a known pharmaceutically acceptable carrier or vehicle such as starch, lactose, carcium carbonate and others in the same manner as the SF-837 substance itself.

According to a second aspect of this invention, there is provided a process for the production of the 9,3'',4''-tri-alkanoyl SF-837 $M_1$ substance of the formula (II).

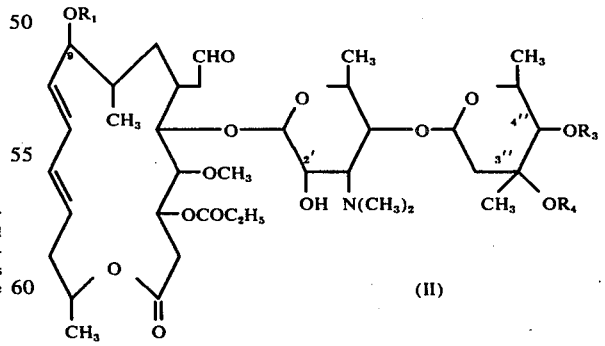

wherein $R_1$ and $R_4$ are each acetyl or propionyl group and $R_3$ is acetyl, propionyl, n-butyryl, isobutyryl or isovaleryl group, which comprises hydrolyzing partially and selectivity a 9,2',3'',4''-tetra-alkanoyl SF-837 $M_1$ substance of the formula (III):

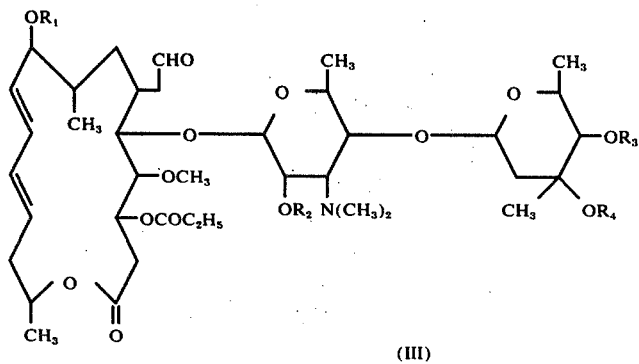

(III)

wherein $R_1$, $R_3$ and $R_4$ are each as defined above and $R_2$ is acetyl or propionyl group, or a 9,18,2',3'',4''-penta-alkanoyl SF-837 $M_1$ substance of the formula (IV):

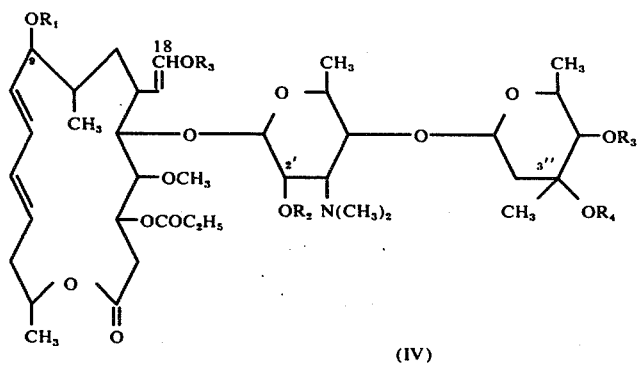

(IV)

wherein $R_1$, $R_2$, $R_3$, and $R_4$ are each as defined above, or a mixture of said 9,2',3'',4''-tetra-alkanoyl SF-837 $M_1$ substance of the formula (III) and said 9,18,2',3'',4''-penta-alkanoyl SF-837 $M_1$ substance of the formula (IV) in an aqueous alkanol or an aqueous acetone to produce the desired 9,3'',4''-tri-alkanoyl SF-837 $M_1$ substance of the formula (II).

According to a preferred embodiment of this second aspect of the invention, there is provided a process for the production of the 9,3'',4''-tri-alkanoyl SF-837 $M_1$ substance of the formula (II'):

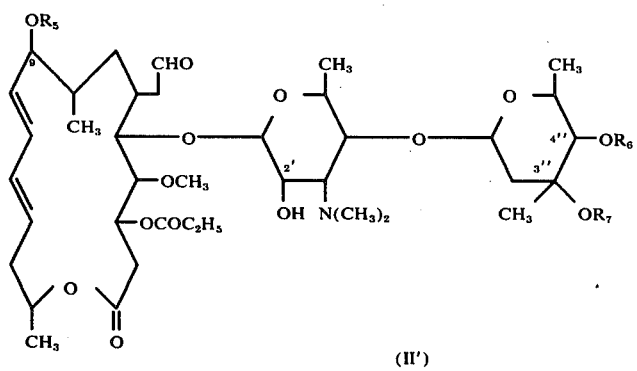

(II')

wherein $R_5$ is acetyl or propionyl group, $R_6$ is acetyl, propionyl, iso-butyryl or iso-valeryl group, and $R_7$ is acetyl or propionyl group, provided that when $R_5$ is acetyl, $R_6$ is acetyl or propionyl, provided that when $R_5$ and $R_7$ are each acetyl, $R_6$ is propionyl, provided that when $R_5$ is acetyl and $R_7$ is propionyl, $R_6$ is acetyl, propionyl, isobutyryl or isovaleryl, and provided that when $R_5$ is propionyl, $R_6$ is acetyl or propionyl and $R_7$ is propionyl group, which comprises hydrolyzing partially and selectively a 9,2',3'',4''-tetra-alkanoyl SF-837 $M_1$ substance of the formula (III'):

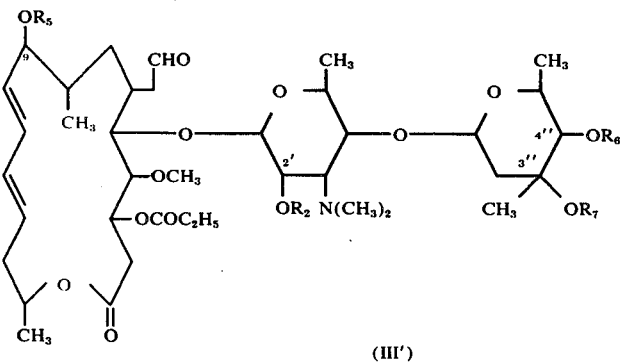

(III')

wherein $R_5$, $R_6$ and $R_7$ are as defined above and $R_2$ is acetyl or propionyl group, or a 9,18,2',3'',4''-penta-alkanoyl SF-837 $M_1$ substance of the formula (IV'):

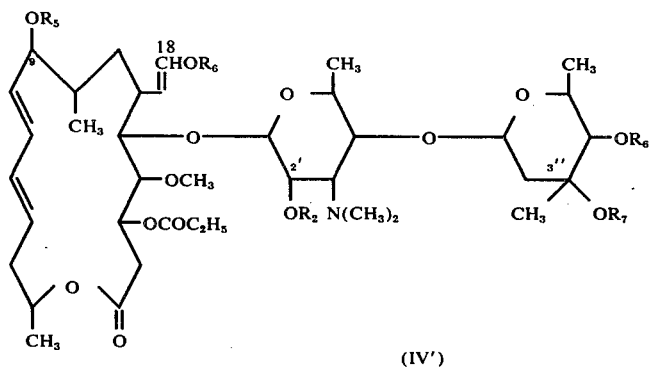

(IV')

wherein $R_2$, $R_5$, $R_6$ and $R_7$ are each as defined above, or a mixture of said 9,2',3'',4''-tetra-alkanoyl SF-837 $M_1$ substance of the formula (III') and said 9,18,2',3'',4''-penta-alkanoyl SF-837 $M_1$ substance of the formula (IV') in an aqueous alkanol of 1–4 carbon atoms or an aqueous acetone to produce the desired 9,3'',4''-tri-alkanoyl SF-837 $M_1$ substance of the formula (II').

In the process of the second aspect of the invention, the partial and selective hydrolysis of the starting 9,2',-3'',4''-tetra-alkanoyl SF-837 $M_1$ substance of the formula (III) or (III') and/or the starting 9,18,2',3'',4''-penta-alkanoyl SF-837 $M_1$ substance of the formula (IV) of (IV') may be carried out with the preferential removal or clevage of the 2'-alkanoyl group ($R_2$) and occasionally with the preferential removal of the 18-alkanoyl group ($R_3$ or $R_5$ at the 18-position), in such a way that the starting 9,2',3'',4''-tetra-alkanoyl SF-837 $M_1$ substance (III) or (III') and/or the starting 9,18,2',-3'',4''-penta-alkanoyl SF-837 $M_1$ substance is dissolved in the aqueous medium consisting of an aqueous alkanol, preferably an alkanol of 1–4 carbon atoms containing a proportion of water, for example, aqueous methanol, aqueous ethanol, aqueous propanol, aqueous butanol or aqueous acetone, and then the resultant solution is heated or allowed to stand at a temperature of from ambient temperature to 100° C. This hydrolysis reaction may be completed in 2–4 days at ambient temperature, while it may be finished in 6–10 hours or less at an elevated temperature of from 60° C to the boiling point of the solvent used.

When the selective hydrolysis of the 9,18,2',3'',4''-penta-alkanoyl SF-837 $M_1$ substance (IV) or (IV') is involved, this hydrolysis may be effected either by allowing at first a solution containing the 9,18,2',3'',4''-penta-alkanoyl SF-837 $M_1$ substance in the aqueous medium such as an aqueous acetone and an aqueous alkanol to stand at ambient temperature to effect the preferential removal of the 2'-alkanoyl group, followed by heating the partially hydrolyzed reaction mixture at an elevated temperature of 60°–100° C to effect the removal of the 18-alkanoyl group; or by heating the solution containing the 9,18,2',3'',4''-penta-alkanoyl SF-837 $M_1$ substance initially at an elevated temperature of 60°–100° C, preferably in the presence of a small quantity (e.g. 1–10% by weight) of a weak base such as alkali meta hydrogen carbonate, for example, sodium hydrogen carbonate; and a tertiary amine, for example, tri-ethylamine, pyridine, N-methylpiperazine, N-methylmorpholine and the like to effect the preferential removal of both the 2'-alkanoyl group and the 18-alkanoyl group at once. A mixture of the 9,2',3'',-4''-tetra-alkanoyl SF-837 $M_1$ substance (III) or (III') and the 9,18,2',3'',4''-penta-alkanoyl SF-837 $M_1$ substance (IV) or (IV') may be hydrolyzed selectively into the desired 9,3'',4''-tri-alkanoyl SF-837 $M_1$ substance (II) or (II') by heating a solution of said mixture in the aqueous medium at an elevated temperature of 60°–100° C in the presence of a weak base such as mentioned in the above. The aqueous alkanol or acetone may suitably contain 10 to 30% by volume of water. The recovery of the desired product (II) or (II') from the reaction mixture may conveniently be conducted by extracting the reaction mixture with an organic solvent such as benzene or ethyl acetate, washing the extract solution of the desired product with water and then concentrating said solution by evaporation of the organic solvent to deposit the described product.

The 9,2′,3″,4‴-tetra-alkanoyl SF-837 M₁ substance of the formula (III) or (III′) and the 9,18,2′,3″,4‴-penta-alkanoyl SF-837 M₁ substance of the formula (IV)

9,2′-di-acetyl SF-837 substance, 9-propionyl SF-837 substance and 9,2′-dipropionyl SF-837 substance represented by the general formula (V):

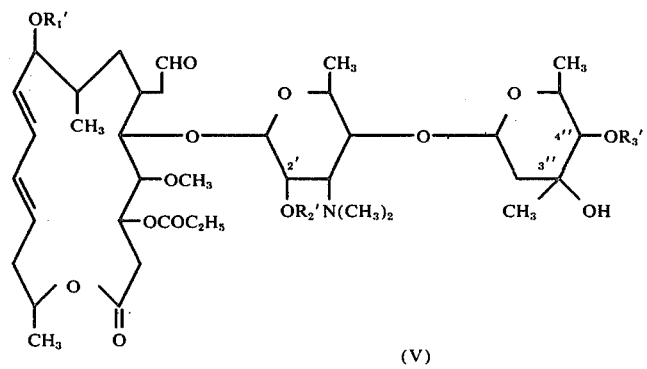

(V)

or (IV′) which are employed as the starting material in the process of the second aspect of the invention are new compounds themselves. In general, they may be prepared by reacting an appropriate alkanoic acid anhydride with an initial material selected from the SF-837 substance (see the "Journal of Antibiotic" Vol. 24, page 460 (1971), 9,2′-di-acetyl SF-837 substance, 9-propionyl SF-837 substance, 9,2′-dipropionyl SF-837 substance and 9,2′,4‴-tri-acetyl SF-837 M₁substance (known as disclosed in the "Journal of Antibiotics" Vol. 24, Vol. 457, 473 and 534, respectively (1971), the reaction for acylation of said initial substance being effected at a temperature of 50°-120° C in an organic solvent in the presence of an organic base of amine type, for example, pryidine, quinoline, α-picoline, diethylaniline, N-ethylmorpholine and triethylamine. Through our research, we have found that the 9- and 2′-hydroxyl groups of the SF-837 substance as well as the 9-, 2′- and 4‴-hydroxyl groups of the SF-837 M₁ substance are relatively much reactive for the acylation with an alkanoic acid anhydride such as acetic anhydride or propionic anhydride, that the tertiary 3″-hydroxyl group of the SF-837 substance or of the SF-837 M₁ substance is relatively less reactive for the acylation, and that when the SF-837 substance is acylated by reacting with an alkanoic acid anhydride such as acetic anhydride at an elevated temperature of e.g., 50°-120° C in the presence of an appropriate organic base such as pyridine under anhydrous conditions, the 9- and 2′-hydroxyl groups thereof are readily acylated with said alkanoic acid anhydride and the 4‴-propionyl group of the SF-837 substance is shifted to the 3″-hydroxyl group to convert the latter into the 3″-propionyloxy group, while the 4‴-position is acylated with said alkanoic acid anhydride with concomitant shift of the 4‴-propionyl group to 3″-position. When the 9,2′-di-acetyl or 9,2′-dipropionyl SF-837 substance or the 9,2′,4‴-tri-acetyl SF-837 M₁ substance is acylated with an alkanoic acid anhydride in the same manner as stated just above the shift of the 4‴-propionyl group of the 4‴-acetyl group to the 3″-hydroxyl group takes place concurrently with the acylation of the 4‴-position with said alkanoic acid anhydride.

Accordingly, the preparation of the starting 9,2′,3″,4‴-tetra-alkanoyl SF-837 M₁ substance of the formula (III) may generally be achieved by acylating an initial material selected from the group consisting of SF-837 substance, 9,2′,4‴-tri-acetyl SF-837 M₁ substance, 9,2′-di-acetyl SF-837 substance, 9-propionyl SF-837 substance and 9,2′-dipropionyl SF-837 substance represented by the general formula (V):

wherein $R_1'$, $R_2'$ and $R_3'$ are each a hydrogen atom or acetyl or propionyl group, with an alkanoic acid anhydride of the formula (VI):

$R_3-O-R_3$ (VI)

wherein $R_3$ is acetyl, propionyl, n-butyryl, isobutyryl or isovaleryl group at a temperature of 50° to 120° C and in the presence of an organic base of the type as mentioned above. If desired, an appropriate organic solvent which is inert to the reagents employed and the reaction products formed may be used as the reaction medium for the acylation. When the SF-837 M₁ substance or the SF-837 substance of the general formula (V) where $R_1'$ and $R_2'$ are both hydrogen is employed as the initial substance to be acylated with the alkanoic acid anhydride, (VI), the alkanoic acid anhydride (VI) should be selected from acetic anhydride and propionic anhydride.

The preparation of the starting 9,18,2′,3″,4‴-penta-alkanoyl SF-837 M₁ substance of the formula (IV) may be achieved in a similar way by acylating the SF-837 M₁ substance, SF-837 substance, 9,2′,4‴-tri-acetyl SF-837 M₁ substance, 9,2′-di-acetyl SF-837 substance, 9-propionyl SF-837 substance or 9,2′-dipropionyl SF-837 substance represented by the general formula (V) with an alkanoic acid anhydride of the formula (VI) at a temperature of 50°-120° C for a prolonged time or at a temperature of 100°-120° C and in the presence of an organic base of the amine type as mentioned above. Thus, for instance, 9,2′,4‴-tri-acetyl-3″-propionyl SF-837 M₁ substance and 9,18,2′,,4‴-tetra-acetyl-3″-propionyl SF-837 M₁ substance may be prepared by acylating SF-837 substance with acetic anhydride at a temperature of 50°-120° C in the presence of an organic base of such type as pyridine, quinoline, α-picoline, diethylaniline, N-ethylmorpholine and triethylamine. 9,2′,3″-tri-acetyl-4‴-propionyl SF-837 M₁ substance (namely, 9,2′,3″-tri-acetyl SF-837 substance) and 9,18,2′,3″-tetra-acetyl-4‴-propionyl SF-837 M₁ substance (namely, 9,18,2′,3″-tetra-acetyl SF-837 substance) may be prepared by acylating 9,2′,4‴-tri-acetyl SF-837 M₁ substance with propionic anhydride at a temperature of 50°-120° C in the presence of an organic base of the amine type as mentioned above.

In the process of preparing the 9,2′,3″,4‴-tetra-alkanoyl SF-837 M₁ substance of the formula (III), when the SF-837 M₁ substance [$R_1' = R_2' = R_3' = H$ in respect to the formula (V)] is employed as the initial material to be acylated with the acylating agent of the formula (VI), there is formed, in general, such a 9,2′,3″,4″-tetra-alkanoyl SF-837 $M_1$ substance of the formula (III) where the four alkanoyl groups in the 9-, 2′-, 3″- and 4″-positions are identical to each other and are the same as the alkanoyl residue of the acylating agent employed. When the SF-837 substance is employed as the initial material to be acylated with the acylating agent of the formula (VI), this acylating agent employed should be acetic anhydride or alternatively propionic anhydride and there is formed such a 9,2′,3″,4″-tetra-alkanoyl SF-837 $M_1$ substance of the formula (III) where the 3″-alkanoyl group is the propionyl group shifted from the 4″-position but the 9-, 2′- and 3″-alkanoyl groups present therein are identical to each other and are same as the acetic or propionic residue of the acylating agent of the formula (VI) employed. In case the 9,2″-di-acetyl SF-837 substance or 9,2′-dipropionyl SF-837 substance is employed as the initial material to be acylated with the acylating agent of the formula (VI), this acylating agent employed may be such one of the formula (VI), where $R_3$ is acetyl, propionyl, n-butyryl, isobutyryl or isovaleryl group, and there is formed such a 9,2′, 3″,4″-tetra-alkanoyl SF-837 $M_1$ substance of the formula (III) where the 3″-alkanoyl group is the propionyl group shifted from the 4″-position, the 9- and 2′-alkanoyl groups are the same acetyl or propionyl groups and the 4″-alkanoyl group is identical to the alkanoyl residue of the acylating agent employed. When the 9,2′,3″-tri-acetyl SF-837 $M_1$ substance is used as the initial material to be acylated, the acylating agent employed may be such one of the formula (VI) where $R_3$ is acetyl, propionyl, n-butyryl, isobutyryl or isovaleryl group, and there is formed such a 9,2′,3″,4″-tetra-alkanoyl SF-837 $M_1$ substance of the formula (III) where the 9-, 2′- and 3″-alkanoyl groups are the same acetyl group and the 4″-alkanoyl group is identical to the alkanoyl residue of the acylating agent employed.

The acylation of the initial material of the formula (V) with the acylating agent compound of the formula (VI) may conveniently be carried out in an organic solvent which is inert to the acylation reaction and which may preferably be a relatively higher boiling organic solvent such as diglyme (namely bis-(2-methoxyethyl)ether), ethyleneglycol dimethylether and toluene. Of course, a lower boiling organic solvent such as benzene may be used as the reaction solvent, if the reaction pressure is higher. An excess of pyridine which is employed as the above-mentioned organic base of the amine type may occasionally serve as the reaction solvent, too. On the other hand, an excess of the alkanoic acid anhydride which is employed as the acylating agent, such as acetic anhydride and propionic anhydride may also be utilized as the reaction solvent, provided that a sufficient amount of the organic base is present in the reaction system. The alkanoic acid anhydride of the formula (VI) used as the acylating agent may be acetic anhydride, propionic anhydride, n-butanoic acid anhydride, iso-butanoic acid or isovaleric anhydride. Instead of these acid anhydrides, there may equally be employed a functional equivalent reagent such as the acid anhydride of the formula (VI), for example, a mixture of the acid chloride and a metal salt of the corresponding acid.

The reaction temperature for the acylation may generally be an elevated temperature of 50°–120° C. When the reaction temperature exceeds 100° C, increased amounts of undesired by-products are likely to be formed. On the other hand, when the reaction temperature is less than 50° C, the reaction time required to complete the acylation is about 7 days. It is desirable, therefore that the acylation should be conducted at a temperature of 80°–100° C and for a reaction time of 10–20 hours. When the initial material of the formula (V) is acylated with the alkanoic acid anhydride of the formula (VI) at a reaction temperature of 65°–85° C for a reaction time of 10–15 hours using the acylating agent (VI) in a proportion of 1.5 to 2.0 equivalents to the initial material (V), the 9,2′,3″,4″-tetra-alkanoyl SF-837 $M_1$ substance (III) are formed substantially exclusively but the 9,18,2′,3–,4″-penta-alkanoyl SF-837 $M_1$ substance (IV) is substantially not formed. When the acylation is effected at a temperature of 85°–95° C, the 9,2′,3″,4″-tetra-alkanoyl SF-837 $M_1$ substance of the formula (III) is formed as the main product and the 9,18,2′,3″4″-penta-alkanoyl SF-837 $M_1$ substance of the formula (IV) is formed as a minor product. When the acylation is carried out at a relatively higher temperature of e.g. 110°–120° C and for a relatively long time, the 18-aldehyde group in the lactone ring of the initial material (V) can be acylated, to give an increased proportion of the 9,18,2′,3″,4″-penta-alkanoyl SF-837 $M_1$ substance (VI).

The 9,2′,3″,4″-tetra-alkanoyl SF-837 $M_1$ substance (III) or the 9,18,2′,3″,4″-penta-alkanoyl SF-837 $M_1$ substance (IV) or a mixture thereof which has been prepared in the above-mentioned way may then be recovered from the acylation reaction mixture by separating therefrom the excess of the unreacted acylating agent, the unreacted initial material and the reaction solvent. For this purpose, it is convenient that the acylation reaction mixture is admixed with an equal volume or more of benzene or toluene or ethyl acetate together with an amount of water and aqueous sodium hydrogen carbonate, the resulting admixture is well agitated to transfer the acylation products into the benzene or toluene or ethyl acetate layer, this benzene or toluene or ethyl acetate layer containing the acylation products in solution is removed from the aqueous phase of the admixture and then washed with aqueous sodium hydrogen carbonate and with water and subsequently concentrated to dryness by evaporation of the organic solvent to deposit the acylation products of the SF-837 substance. In this way, the 9,2′,3″,4″-tetra-alkanoyl SF-837 $M_1$ substance (III) may be recovered from the acylation reaction mixture. In case the acylation reaction mixture contains a proportion of the 9,18,2′,3″,4″-penta-alkanoyl SF-837 $M_1$ substance (IV), a mixture of the 9,2′,3″,4″-tetra-alkanoyl SF-837 $M_1$ substance (III) and the 9,18,2′,3″,4″-penta-alkanoyl SF-837 $M_1$ substance (IV) may be recovered in the aforesaid recovery procedure. The 9,2′,3″,4″-tetra-alkanoyl SF-837 $M_1$ substance (III) recovered may further be purified by chromatographying in a silica gel column with a mixture of benzene-acetone as the development solvent or by recrystallizing from isopropanol or by a combination of these purification procedures. The isolation of the 9,2′,3″,4″-tetra-alkanoyl SF-837 $M_1$ substance (III) from the 9,18,2′,3″,4″-penta-alkanoyl SF-837 $M_1$ substance (IV) may be achieved by subjecting the mixture of these substances to a conventional column chromatography over silica gel with benzene-acetone as the development solvent. If desired, however, it is possible that the mixture of the 9,2′,3″,4″-tetra-alkanoyl SF-837 $M_1$ substance (III) and the 9,18,2',3'',4''-penta-alkanoyl SF-837 M₁ substances (IV) as such is employed as the starting material to be hydrolyzed partially and selectively in the process of the second aspect of this invention, because both these two substances (III) and (IV) equally give the desired 9,3'',4''-tri-alkanoyl SF-837 M₁ substance of the formula (II) upon the selective removal of the 2'-alkanoyl group and the 18-alkanoyl group therefrom according to the process of the second aspect of this invention.

According to a third aspect of this invention, there is provided a process for the production of the 9,3'',4''-tri-alkanoyl SF-837 M₁ substance of the aforesaid formula (II), which comprises (i) acylating an initial material selected from the group consisting of SF-837 substance, 9,2',4''-tri-acetyl SF-837 M₁ substance, 9,2'-di-acetyl SF-837 substance, 9-propionyl SF-837 substance and 9,2'-dipropionyl SF-837 substance represented by the aforesaid formula (V), with an alkanoic acid anhydride of the aforesaid formula (VI) at a temperature of 50° to 120° C and in the presence of an organic base such as pyridine, quinoline, α-picoline, diethylaniline, N-ethylmorpholine and triethylamine for a sufficient time to produce a 9,2',3'',4''-tetra-alkanoyl SF-837 M₁ substance of the aforesaid formula (III) or a 9,18,2',3'λ',4''-penta-alkanoyl SF-837 M₁ substance of the aforesaid formula (IV) or a mixture of these substances (III) and (IV), and (ii) hydrolyzing partially and selectively the 9,2',3'',4''-tetra-alkanoyl SF-837 M₁ substance of the above formula (III) or the 9,18,2',3'',4''-penta-alkanoyl SF-837 M₁ substance of the formula (IV) or a mixture of these substances (III) and (IV) in an aqueous alkanol or an aqueous acetone to produce the desired 9,3'',4''-tri-alkanoyl SF-837 M₁ substance of the formula (II).

According to the fourth aspect of this invention, there is provided a pharmaceutical composition suitable for use in treating bacterial infections in a living animal, comprising a therapeutically effective amount of a 9,3'',4''-tri-alkanoyl SF-837 M₁ substance of the aforesaid formula (II) or (II') and/or a pharmaceutically acceptable salt of the 9,3'',4''-tri-alkanoyl SF-837 M₁ substance, in combination with a pharmaceutically acceptable carrier.

The present invention is now illustrated with reference to the following Examples to which the invention is not limited.

EXAMPLE 1 a. SF-837 substance (10 g) was dissolved in a mixture of 60 cc of pyridine and 30 cc of acetic anhydride, and the resulting solution was heated at 100° C for 10.5 hours and then allowed to stand at ambient temperature for 1 day to complete the acylation reaction. A sample taken from the reaction mixture was examined by a thin layer chromatography on silica gel plate using a mixture of benzene-acetone (4:1) as the development solvent (colored by sulfuric acid), and it was then observed that the acylation products of the SF-837 substance contained 9,2',4''-tri-acetyl-3''-propionyl SF-837 M₁ substance as the main ingredient and minor proportions of 9,2'-di-acetyl SF-837 substance and of 9,18,2'4''-tetra-acetyl-3''-propionyl SF-837 M₁ substance.

The reaction mixture was concentrated to dryness under reduced pressure, and the residue was extracted with benzene and then the resulting benzene extract was washed with benzene. The benzene extract so obtained was concentrated to dryness, and the residue was taken into a small volume of benzene. The resulting solution in benzene was passed through a column of silica gel, which was then developed with a mixed solvent of benzene-acetone (14:1). The eluate was collected in 10 ml fractions. The fraction Nos. 55 to 80 were combined together and concentrated to dryness to give 2.5 g of a powder product of 9,18,2',4''-tetra-acetyl-3''-propionyl SF-837 M₁ substance.

| Melting point | 105–110° C |
|---|---|
| Molecular weight (as determined by mass spectrometry): | 981 |
| N.M.R. spectrum (in deuterochloroform): | No signal of the group —CHO was observed. |

This product had substantially no antibacterial activity.

b. The fraction Nos. 90 to 135 of the above eluate were combined together and concentrated to dryness to tive 4.9 g of a powder consisting of 9,2',4''-tri-acetyl-3''-propionyl SF-837 M₁ substance. This powder was crystallized from isopropanol to yield purified 9,2',4''-tri-acetyl-3''-propionyl SF-837 M₁ substance having the following properties:

| Melting point: | 218–222° C (with decomposition and coloration) |
|---|---|
| Molecular weight (as determined by mass spectrometry): | 939 |
| N.M.R. spectrum (in deutrochloroform): | Signal of the group —CHO at 9.65 |

This product had an antibacterial activity but lower than that of 9,4''-di-acetyl-3''-propionyl SF-837 M₁ substance.

c. The fraction Nos. 81 to 89 of the above eluate were combined together and concentrated to dryness to give 1.0 g of a powder comprising a mixture of 9,18,2',4''-tetra-acetyl-3''-propionyl SF-837 M₁ substance and 9,2',4''-tri-acetyl-3''-propionyl SF-837 M₁ substance.

d. The 9,2',4''-tri-acetyl-3''-propionyl SF-837 M₁ substance (4.0 g) obtained in the above procedure (b) was dissolved in 50 cc of aqueous 90% methanol (that is, methanol containing 10% by volume of water), and the resulting solution was heated at 60° C for 10 hours to effect the partial and selective hydrolysis of said 9,2',4''-tri-acetyl-3''-propionyl SF-837 M₁ substance. The reaction mixture so obtained was admixed with large volumes of water and benzene, and the aqueous layer of the resulting admixture was adjusted to pH 8 by addition of aqueous sodium hydrogen carbonate. The admixture was then shaken vigorously and then left to stand for a while. The benzene phase was separated from the aqueous phase, washed with water and then concentrated to dryness to give 3.6 g of a crystalline product of 9,4''-di-acetyl-3''-propionyl SF-837 M₁ substance. This product was recrystallized from isopropanol to give a product having the following properties:

| Melting point: | 228–230° C (with decomposition) |
|---|---|
| Molecular weight (as | |

| | |
|---|---|
| determined by mass spectrometry): | 897 |
| Specific optical rotation: | $[\alpha]_D^{22}$ −60.0° (1%, $CHCl_3$) |
| N.M.R. spectrum (in deuterochloroform): | Signal of the group —CHO at 9.67 | e. 3.0 g of the mixture of 9,18,2',4''-tetra-acetyl-3''-propionyl SF-837 $M_1$ substance and 9,2',4''-tri-acetyl-3''-propionyl SF-837 $M_1$ substance obtained in the above procedure (c) was dissolved in 300 cc of aqueous 80% ethanol (namely, ethanol containing 20% by volume of water), and the resulting solution was heated at 80° C for 20 hours for the partial and selective hydrolysis. The reaction mixture so obtained was then adjusted to pH 8.0 by addition of aqueous sodium hydrogen carbonate and subsequently extracted with benzene. The resultant extract in benzene was washed with water and concentrated to dryness to obtain 2.0 g of a crystalline product of 9,4''-di-acetyl-3''-propionyl SF-837 $M_1$ substance. This product was recrystallized from isopropanol to give a product having the same properties as mentioned in the procedure (d).

f. 0.6 g of the 9,18,2',4''-tetra-acetyl-3''-propionyl SF-837 $M_1$ substance obtained in the above procedure (a) was dissolved in 100 cc of 90% aqueous methanol, and the resulting solution was allowed to stand at ambient temperature overnight. A large part of the above-mentioned acylated SF-837 $M_1$ substance was converted into 9,18,4''-tri-acetyl-3''-propionyl SF-837 $M_1$ substance which had a melting point of 113°–116° C and a molecular weight of 939 as measured by mass spectrometry. This product had no antibacterial activity. This 9,18,4''-tri-acetyl-3''-propionyl SF-837 $M_1$ substance (0.5 g) was again dissolved in 20 cc of aqueous 80% ethanol containing 5% by volume of triethylamine, and the resulting solution was heated on a water bath for 6 hours under reflux to effect the removal of the 18-acetyl group by the hydrolysis. The reaction mixture so obtained was concentrated to dryness under reduced pressure to afford 0.45 g of a colorless crystalline product of 9,4''-di-acetyl-3''-propionyl SF-837 $M_1$ substance. This product was recrystallized from isopropanol to give a product of 9,4''-di-acetyl-3''-propionyl SF-837 $M_1$ substance, m.p. 228° to 230° C (with decomposition).

EXAMPLE 2 a. 9,2',4''-tri-acetyl SF-837 $M_1$ substance (2 g) (which was known as 2',4'',9-tri-O-acetyl-4''-depropionyl SF-837 as described in the "Journal of Antibiotics" Vol. 24, pages 534–535 (1971) was admixed with a mixture of 8 cc of pyridine and 8 cc of propionic anhydride, and the admixture was heated at 100° C for 50 hours. The reaction mixture was poured into a large volume of ice-water, which was then extracted three times with 100 cc portions of benzene. The resulting extracts in benzene were combined together, dried over anhydrous sodium sulfate and then concentrated.

The concentrated solution was chromatographed in a column of silica gel (3 × 20 cm) using a mixture of benzene-acetone (15:1) as the development solvent. The eluate from the column was collected in 10 g fractions. The fraction Nos. 25–33 were combined together and concentrated to give 800 mg of a powder product of 9,2',3''-tri-acetyl-4''-propionyl SF-837 $M_1$ substance (namely, 9,2',3''-tri-acetyl SF-837 substance.)

| | |
|---|---|
| Melting point: | 90–95° C (moistened) |
| Molecular weight (as determined by mass spectrometry): | 939 | b. The purified 9,2', ,3''-tri-acetyl-4''-propionyl SF-837 $M_1$ substance (800 mg) obtained in the above procedure (a) was dissolved in 30 cc of aqueous 90% methanol (that is, methanol containing 10% by volume of water), and the resulting solution was allowed to stand at 40° C overnight to effect the hydrolysis. The reaction mixture was concentrated under reduced pressure, and the syrupy residue was admixed with isopropanol to deposit 600 mg of a crystalline product of 9,3''-di-acetyl-4''-propionyl SF-837 $M_1$ substance (that is, 9,3''-di-acetyl SF-837 substance). This product was recrystallized from isopropanol to afford a pure product having the following properties:

| | |
|---|---|
| Melting point: | 198–203° C (with decomposition) |
| Molecular weight (as determined by mass spectrometry): | 897 | c. The fraction Nos. 6–22 obtained from the column chromatography which was effected in the above procedure (a) were combined together and concentrated to give 850 mg of a powder comprising a mixture of 9,18,2',3''-tetra-acetyl SF-837 substance and 9,2',3''-tri-acetyl SF-837 substance. This powder was dissolved into 40 cc of 80% aqueous ethanol containing 5% by volume of triethylamine, and the resulting solution was heated at 65° C for 8 hours for the partial hydrolysis. The reaction mixture so obtained was concentrated and the syrupy residue was admixed with 5 cc of isopropanol to deposit 400 mg of a powder of 9,3''-di-acetyl SF-837 substance as a further crop. m.p. 198°–203° C (dec.).

EXAMPLE 3 a. 9,2'-di-acetyl SF-837 substance (1.0 g) was dissolved in a mixture of 5 cc of pyridine and 4 cc of acetic anhydride, and the resulting solution was heated at 105°–110° C for 60 hours for the acetylation of the 9,2'-di-acetyl SF-837 substance. The acylation reaction mixture was then poured into a large volume of ice-water, which was then extracted twice with 100 cc portions of benzene. The combined benzene extracts were washed with an aqueous solution of 5% potassium hydrogen sulfate, then with a saturated aqueous solution of sodium hydrogen carbonate and finally with water. The benzene solution (the washed extracts) was concentrated to dryness to give 0.9 g of a colorless powder product comprising 9,18,2',4''-tetra-acetyl-3''-propionyl SF-837 $M_1$ substance.

b. The purified 9,18,2',4''-tetra-acetyl-3''-propionyl SF-837 $M_1$ substance (0.98 g) obtained in the above procedure (a) was dissolved in 80 cc of aqueous 80% ethanol containing 5% by volume of triethylamine, and the resulting solution was heated for 8 hours under reflux for the hydrolysis. The reaction mixture was concentrated to dryness to give 0.8 g of a crystalline product of 9,4''-di-acetyl-3''-propionyl SF-837 $M_1$ substance. m.p. 228°–230° C (dec.).

EXAMPLE 4 a. 9-propionyl SF-837 substance (20 g) was dissolved in a mixture of 80 cc of pyridine and 40 cc of acetic anhydride, and the resulting solution was heated at 100° C for 20 hours for the acylation of the 9-propionyl SF-837 substance. The reaction mixture so obtained was then poured into 200 cc of water containing 50 g of ice, which was then neutralized by addition of aqueous sodium carbonate and extracted three times with 100 cc portions of ethyl acetate. The resulting extracts in ethyl acetate were combined together, dried over anhydrous sodium sulfate and concentrated by evaporation of the solvent to give 21 g of a syrupy residue comprising 9-propionyl-2',4''-di-acetyl-3''-propionyl SF-837 $M_1$ substance and a minor proportion of 9-propionyl-18,2',4''-tri-acetyl-3''-propionyl SF-837 $M_1$ substance.

b. The syrupy residue obtained in the above procedure (a) was poured into 280 cc of aqueous 90% methanol, and the resulting solution was heated at a temperature of 65° C for 5 hours, admixed with 6 cc of triethylamine and then heated at a temperature of 65° C for further 9 hours. The hydrolysis reaction mixture so obtained was concentrated to dryness and the residue was dissolved in 30 cc of isopropanol. The resulting solution was allowed to cool and stand, depositing a crystalline product. This product (12 g) was collected by filtration and identified as 9-propionyl-4''-acetyl-3''-propionyl SF-837 $M_1$ substance. This product was recrystallized from isopropanol to afford a product having a melting point of 205°–208° C (dec.) and a molecular weight of 911 as determined by mass spectrometry.

EXAMPLE 5

9,2'-di-acetyl SF-837 substance (1.0 g) was dissolved in a mixture of 50 cc of pyridine and 10 cc of isobutanoic anhydride, and the resulting solution was heated at 100° C for 48 hours. The reaction mixture so obtained which contained 9,2'-di-acetyl-4''-isobutyryl-3''-propionyl SF-837 $M_1$ substance and a minor proportion of 9,2'-di-acetyl-18,4''-di-isobutyryl-3''-propionyl SF-837 $M_1$ substance was subsequently processed in the same manner as Example 4 (a) and (b), yielding 0.25 g of a powdery product of 9-acetyl-4''-isobutyryl-3''-propionyl SF-837 $M_1$ substance. This powder product showed a melting point of 140°–145° C (moistened) and a molecular weight of 925 as determined by mass spectrometry.

EXAMPLE 6

9,2'-di-acetyl SF-837 substance (1.0 g) was dissolved in 50 cc of pyridine, to which was then added 10 cc of isovaleric anhydride. The mixture was heated at 100° C for 48 hours. The acylation reaction mixture so obtained containing 9,2'-di-acetyl-4''-isovaleryl-3''-propionyl SF-837 $M_1$ substance and a minor proportion of 9,2'-di-acetyl-18,4''-di-isovaleryl-3''-propionyl SF-837 $M_1$ substance was subsequently processed in the same manner as in Example 4 (a) and (b) to obtain 0.2 g of a powder of 9-acetyl-4''-isovaleryl-3''-propionyl SF-837 $M_1$ substance.

| | |
|---|---|
| Melting point: | 135–140° C (moistened) |
| Molecular weight (as determined by mass spectrometry): | 939 |
| N.M.R. spectrum (in deuterchloroform): | Signal of the group —CHO at 9.67 |

EXAMPLE 7 a. SF-837 substance (100 g) was dissolved in a mixture of 600 cc of pyridine and 300 cc of acetic anhydride, and the resultant solution was heated at 100° C for 23 hours for the acetylation of SF-837 substance. The reaction mixture so obtained was poured into 2.5 l of ice-water, which was then neutralized by addition of aqueous sodium hydrogen carbonate and subsequently extracted with 1 l of benzene. The benzene extract so obtained was washed with an aqueous solution of 10% potassium hydrogen sulfate, then with a saturated aqueous solution of sodium hydrogen carbonate and finally with water and was subsequently dried over anhydrous sodium carbonate, followed by concentrating under reduced pressure. A syrupy residue (120 g) comprising 9,2',4''-tri-acetyl-3''-propionyl SF-837 $M_1$ substance and a minor proportion of 9,18,2',4''-tetra-acetyl-3''-propionyl SF-837 $M_1$ substance was obtained.

b. The residue obtained in the above procedure (a) was dissolved in 500 cc of aqueous 80% methanol, and the resulting solution was allowed to stand at 60° C for 7 hours. The reaction solution was then left to deposit 41 g of a crystalline product of 9,4''-di-acetyl-3''-propionyl SF-837 $M_1$ substance. m.p. 228°–230° C (dec.).

c. The mother liquor from which said crystalline product was removed was then concentrated and admixed with 300 cc of aqueous 80% ethanol and 20 cc of triethylamine. The admixture so obtained was heated at 65° C for 8 hours for the partial hydrolysis. The reaction mixture so obtained was allowed to stand in cold, depositing a further 39 g of a crystalline product of 9,4''-di-acetyl-3''-propionyl SF-837 $M_1$ substance. m.p. 228°–230° C (dec.).

EXAMPLE 8 a. Isovaleric acid (18.6 g) was dissolved in 100 cc of methanol containing 9.2 g of sodium hydroxide, and the resulting solution was concentrated to dryness and the solid residue was then taken in an amount of benzene. The mixture was again concentrated to dryness, and the residue was admixed with 22 g of isovaleryl chloride under cooling. After 1 hour, the admixture obtained was mixed with 12 g of 9,2'-di-acetyl SF-837 substance and then heated at 100° C for 56 hours. The acylation reaction mixture so obtained containing 9,2'-di-acetyl-4''-isovaleryl-3''-propionyl SF-837 $M_1$ substance and a minor proportion of 9,2',18-tri-acetyl-4''-isovaleryl-3''-propionyl SF-837 $M_1$ substance was poured into a large volume of ice-water, which was subsequently neutralized by addition of sodium hydrogen carbonate and then extracted with 250 cc of benzene. The benzene extract was washed with water and concentrated. The resulting concentrated solution was passed into a column of silica gel (4 × 28 cm) for chromatography, and the column was developed with benzene-acetone (20:1 by volume). The eluate from the silica gel column was collected in 8 cc fractions. The fraction Nos. 43–53 were combined together and concentrated to dryness to give 3.6 g of a residue mainly comprising 9,2'-di-acetyl-4''-isovaleryl-3''-propionyl SF-837 M₁ substance.

b. The 9,2'-di-acetyl-4''-isovaleryl-3''-propionyl SF-837 M₁ substance (3.5 g) obtained in the above procedure (a) was dissolved in 100 cc of aqueous acetone (that is, a mixture of acetone and water at a ratio of 7:3 by volume). The resulting solution was heated at a temperature of 50° C overnight under agitation. The hydrolysis reaction mixture so obtained was then concentrated to dryness under reduced pressure to give 3.0 g of a powder product of 9-acetyl-3''-propionyl-4''-isovaleryl SF-837 M₁ substance. m.p. 135°–140° C.

EXAMPLE 9 a. An admixture of 5 g of the 9,2'-di-acetyl SF-837 substance, 100 cc of pyridine and 40 cc of propionic anhydride was heated at 100° C for 16 hours. The reaction mixture in the form of a black colored solution was then poured into a large volume of ice-water, and the aqueous phase of the mixture was adjusted to pH 8.0 by addition of aqueous sodium hydrogen carbonate. The mixture was then extracted with benzene, and the benzene extract was washed with water and concentrated to dryness. The residue was taken up into a small volume of benzene and the benzene solution was chromatographed by passing into a column of silica gel (4 × 20 cm) and developing with a solvent mixture of 10:1 benzene-acetone. The eluate was collected in 8 g fractions, and the fractions Nos. 35–44 were combined together and concentrated to dryness, giving 1.1 g of the 9,2'-di-acetyl-18,3''-di-propionyl SF-837 substance which showed the following properties:

| | |
|---|---|
| Melting point: | 95–101° C (moistened) |
| Molecular weight (determined by mass spectrum analysis): | 1,009 |
| Nuclear magnetic resonance absorption (in CDCl₃): | No signal of the CHO group was observed. |
| Antibacterial activity: | Substantially not observed. |

From the fractions Nos. 47–58 of the eluate was recovered 1.0 g of the 9,2'-di-acetyl-3''-propionyl SF-837 substance which showed the following properties:

| | |
|---|---|
| Melting point: | 106–108° C |
| Molecular weight (determined by mass spectrum analysis): | 953 |
| Nuclear magnetic resonance absorption (in CDCl₃): | Signal of the CHO group at 9.67 was observed. |
| Antibacterial activity: | Lower than that of the 9-acetyl-3''-propionyl SF-837 substance. | b. The 9,2'-di-acetyl-3''-propionyl SF-837 substance (0.5 g) was dissolved in 100 cc of aqueous 90% methanol (a mixture of methanol and water in a ratio of 9:1 by volume), and the solution was heated at 60° C for 8 hours to effect the selective hydrolysis. The reaction mixture was admixed with a large volume of water, neutralized with aqueous sodium hydrogen carbonate and then extracted with ethyl acetate. The resulting ethyl acetate extract was washed with water and concentrated to dryness to afford 0.35 g of 9-acetyl-3'',4''-dipropionyl SF-837 M₁ substance (namely, the 9-acetyl-3''-propionyl SF-837 substance) which showed the following properties:

| | |
|---|---|
| Melting point: | 222–224° C |
| Molecular weight (determined by mass spectrum analysis): | 911 |
| Nuclear magnetic resonance absorption (in CDCl₃): | Signal of the CHO group at 9.68 was observed. | c. Further, the 9,2'-di-acetyl-18,3''-di-propionyl SF-837 substance (1.0 g) was dissolved in 40 cc of aqueous 90% methanol, and the solution was allowed to stand at ambient temperature for 2 days. The reaction solution was then concentrated to dryness, giving 0.85 g of a powdery product of the 9-acetyl-18,3''-di-propionyl SF-837 substance which showed the following properties:

| | |
|---|---|
| Melting point: | 103–106° C |
| Molecular weight (determined by mass spectrum analysis): | 967 |
| Antibacterial activity: | Not observed. |

This 9-acetyl-18,3''-di-propionyl SF-837 substance was dissolved in 60 cc of aqueous 80% ethanol containing 5% tri-ethylamine, and the solution was heated at 80° C for 10 hours. The reaction mixture was neutralized with aqueous sodium hydrogen carbonate and then extracted with benzene. The benzene solution (the extract) was washed with water and concentrated to dryness, affording 0.5 g of a crystalline product of 9-acetyl-3'',4''-dipropionyl SF-837 M₁ substance (namely, 9-acetyl-3''-propionyl SF-837 substance) as another crop.

EXAMPLE 10 a. The SF-837 substance (3.0 g) was dissolved in a mixture of 50 cc of pyridine and 15 cc of propionic anhydride, and the admixture so obtained was heated at 100° C for 16 hours. The reaction mixture was poured into a large volume of ice-water to deposit the acylation products of the SF-837 substance (a mixture of 9,18,2'-3''-tetra-propionyl SF-837 substance and 9,2',3''-tri-propionyl SF-837 substance) which was then collected by filtration and subsequently washed with water.

b. The acylation products so obtained were then immediately dissolved in 100 cc of aqueous 80% ethanol, and to the resulting solution was added 5.0 g of powdered sodium hydrogen carbonate. The mixture was heated at 80° C for 16 hours to effect the hydrolysis reaction. The reaction mixture was passed through a column of active carbon (50 cc) and then extracted with benzene, and the benzene extract was washed with water and concentrated to dryness. There was obtained 0.9 g of an amorphous product of 9,3'',4''-tripropionyl SF-837 M₁ substance (namely, 9,3''-di-propionyl SF-837 substance) which exhibited the following properties:

| | |
|---|---|
| Melting point: | 150–160° C (moistened) |
| Molecular weight (determined by mass spectrum analysis): | 925 |
| Nuclear magnetic resonance | |

| absorption (in CDCl₃): | Signal of the group —CHO at 9.68 |
|---|---|

EXAMPLE 11 a. A mixture of SF-837 substance (180 mg) and propionic anhydride (0.5 ml) in pyridine (5 ml) was shaken in a sealed tube at 28° C for 5 days. The reaction mixture was concentrated to dryness, and the residue was dissolved in chloroform. After washing with water and drying over sodium sulfate, the chloroform layer was evaporated to give a white powder (210 mg). It showed a major spot of Rf 0.6 and a minor spot of Rf 0.5 on silica gel TLC developed with benzene-acetone (5:1). The former was separated from the latter by preparative silica gel plates, using the same solvent system mentioned above.

The main band containing 9,2'-dipropionyl SF-837 substance was extracted with methanol, and the extracts were evaporated to give a white powder (95 mg). Crystallization from carbon tetrachloride gave colorless needles of 9,2'-dipropionyl SF-837 substance (60 mg).

Elemental analysis: Calcd for $C_{47}H_{75}NO_{17}$(M.V'. 951): C 60.95, H 8.16, N 1.51%; Found: C 60.82, H 8.02, N 1.46%.

b. 9,2'-dipropionyl SF-837 substance (4 g) was dissolved in a mixture of 50 ml of pyridine and 50 ml of propionic anhydride, and the mixture was heated at 100° C for 16 hours.

The reaction mixture was poured into a large volume of ice-water, followed by neutralization with sodium hydrogen carbonate.

The acylation products (a mixture of 9,18,2',3''-tetrapropionyl and 9,2',3''-tripropionyl SF-837 substance) were extracted twice with 150 ml portion of benzene. The benzene solution thus obtained was evaporated under reduced pressure.

c. The residue so obtained was then dissolved in 100 ml of aqueous 80% ethanol containing 5 g of sodium hydrogen carbonate.

The mixture was heated at 80° C for 16 hours to effect the hydrolysis, removing the 18- and 2'-acyl groups.

The reaction mixture was then passed through a column of activated carbon (50 ml) and then extracted with benzene, and the benzene extract was washed with water and concentrated to dryness. The resulting solid was recrystallized from isopropanol to give a crystalline product of 9,3''-dipropionyl SF-837 substance (2.3 g) which exhibited the following properties.

| Melting point: | 192–195° C (slightly coloured) |
|---|---|
| Molecular weight (determined by mass spectrum analysis): | 925 |

What we claim is:

1. A 9,3'',4'''-tri-alkanoyl SF-837 M₁ substance of the formula (II):

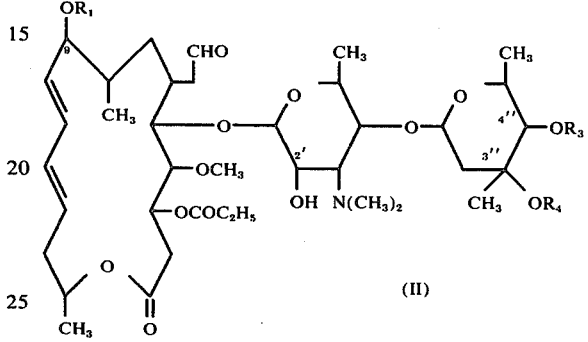

wherein $R_1$ and $R_4$ are each acetyl or propionyl and $R_3$ is acetyl, propionyl, n-butyryl, isobutyryl or isovaleryl.

2. A 9,3'',4'''-tri-alkanoyl SF-837 M₁ substance as claimed in claim 1 which is of the formula (II'):

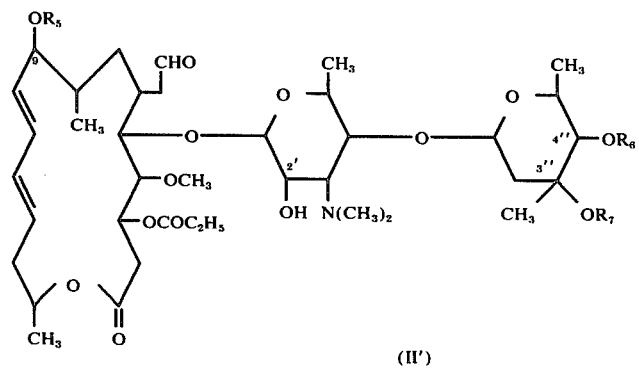

wherein $R_5$ is acetyl or propionyl, $R_6$ is acetyl, propionyl, isobutyryl or isovaleryl, and $R_7$ is acetyl or propionyl, provided that when $R_5$ is acetyl, $R_6$ is acetyl or propionyl, provided that when $R_5$ and $R_7$ are each acetyl, $R_6$ is propionyl, provided that when $R_5$ is acetyl and $R_7$ is propionyl, $R_6$ is acetyl, propionyl, isobutyryl or isovaleryl, and provided that when $R_5$ is propionyl, $R_6$ is acetyl or propionyl and $R_7$ is propionyl.

3. A 9,3'',4'''-tri-alkanoyl SF-837 M₁ substance as claimed in claim 1, which is selected from the consisting of 9,4'''-di-acetyl-3''-propionyl SF-837 M₁ substance; 9,3''-di-acetyl-4'''-propionyl SF-837 M₁ substance; 9-acetyl-4'''-isobutyryl-3''-propionyl SF-837 M₁ substance; 9-acetyl-4'''-isovaleryl-3''-propionyl SF-837 M₁ substance; 9,3''-dipropionyl-4'''-acetyl SF-837 M₁ substance; 9-acetyl-3'',4'''-dipropionyl SF-837 M₁ substance and 9,3'',4'''-tripropionyl SF-837 M₁ substance.

4. A 9,3'',4'''-tri-alkanoyl SF-837 M₁ substance as claimed in claim 1, which is 9,3''-di-acetyl-4'''-propionyl SF-837 M₁ substance.

5. A 9,2′,3″,4″-tetra-alkanoyl SF-837 $M_1$ substance of the formula (III):

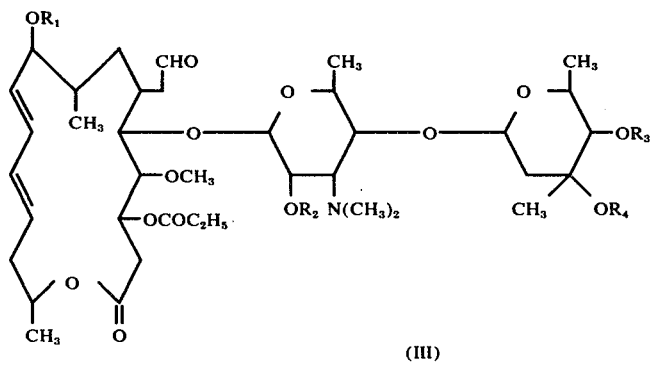

(III)

wherein $R_1$ and $R_4$ are each acetyl or propionyl, $R_2$ is acetyl or propionyl, and $R_3$ is acetyl, propionyl, n-butyryl, isobutyryl or isovaleryl.

6. A 9,18,2′,3″,4″-penta-alkanoyl SF-837 $M_1$ substance of the formula (IV):

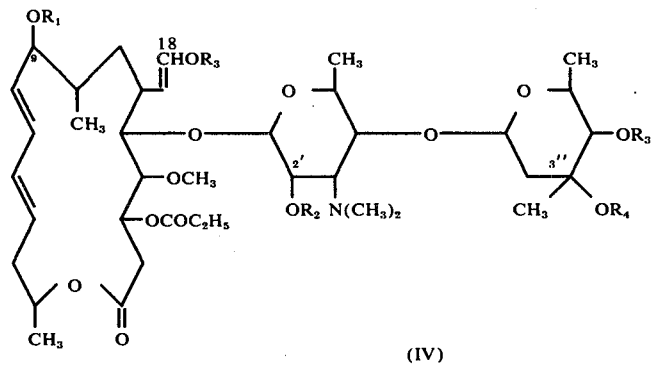

(IV)

wherein $R_1$ and $R_4$ are each acetyl or propionyl, $R_2$ is acetyl or propionyl, and $R_3$ is acetyl, propionyl, n-butyryl, isobutyryl or isovaleryl.

7. A pharmaceutical composition suitable for use in treating bacterial infections in a living animal, comprising a therapeutically effective amount of a compound selected from the group consisting of 9,3″,4″-tri-alkanoyl SF-837 $M_1$ substance of the formula (II) as claimed in claim 1 (and/or), a pharmaceutically acceptable salt thereof and a mixture of said substance and said salt of the 9,3″,4″-tri-alkanoyl SF-837 $M_1$ substance, in combination with a pharmaceutically acceptable carrier.

8. A process for the production of a 9,3″,4″-tri-alkanoyl SF-837 $M_1$ substance of the formula (IT) as defined in claim 1, which comprises
the step (i) of acylating an initial material selected from the group consisting of SF-837 substance, 9,2′,4″-tri-acetyl SF-837 $M_1$ substance, 9,2′-di-acetyl SF-837 substance, 9-propionyl SF-837 substance and 9,2′-dipropionyl SF-837 substance of the formula (V)

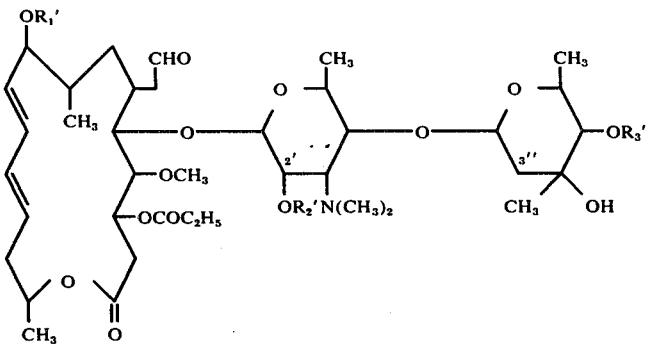

wherein $R_1'$ and $R_2'$ are each a hydrogen atom and $R_3'$ is propionyl; or $R_1'$, $R_2'$ and $R_3'$ are each acetyl; or $R_1'$ and $R_2'$ are each acetyl and $R_3'$ is propionyl; or $R_1'$ and $R_3'$ are each propionyl and $R_2'$ is a hydrogen atom; or $R_1'$, $R_2'$ and $R_3'$ are each propionyl, with an alkanoic acid anhydride of the formula (VI):

$$R_3-O-R_3 \qquad (VI)$$

wherein $R_3$ is acetyl, propionyl, n-butyryl, isobutyryl or isovaleryl group at a temperature of 50° to 120° C and in the presence of an organic base selected from pyridine, quinoline, α-picoline, diethylaniline, N-ethylmorpholine and triethylamine for a sufficient time to produce a 9,2′,3″,4‴-tetra-alkanoyl SF-837 $M_1$ substance of the formula (III):

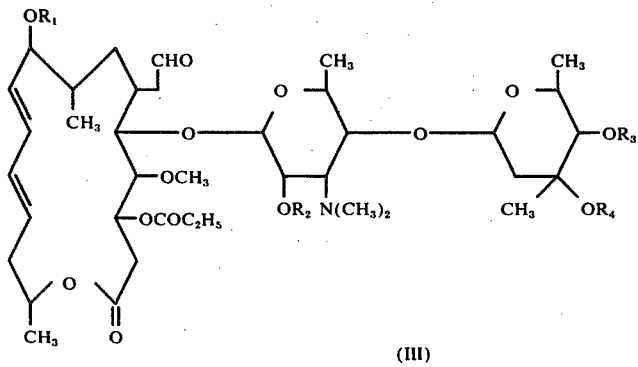

(III)

wherein $R_1$, $R_2$ and $R_4$ are each acetyl or propionyl and $R_3$ is as defined above in the formula (VI), provided that $R_4$ is the same as $R_3'$ initially present at the 4″-position of the initial material employed, or a 9,18,2′,3″,4‴-penta-alkanoyl SF-837 $M_1$ substance of the formula (IV):

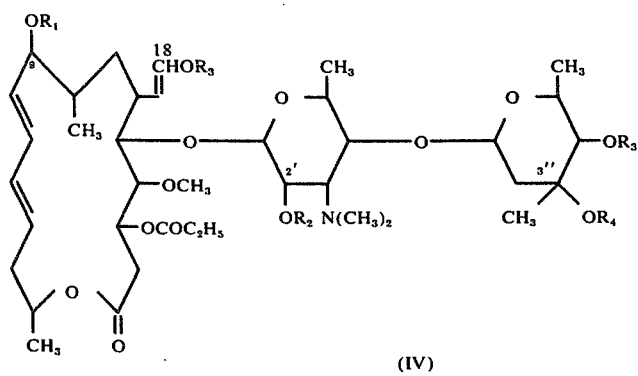

(IV)

wherein $R_1$, $R_2$ and $R_4$ are each acetyl or propionyl and $R_3$ is a defined above in the formula (VI), provided that $R_4$ is the same a $R_3'$ initially present at the 4″-position of the initial material employed, or a mixture of these substances, with concurrent and intermolecular shifting of the alkanoyl group from the 4″-position to the 3‴-position, and the step (ii) of hydrolyzing partially and selectively the 9,2′,3″,4‴-tetra-alkanoyl SF-837 $M_1$ substance of the formula (III) or the 9,18,2′,3″,4‴-penta-alkanoyl SF-837 $M_1$ substance or a mixture of these substances in an aqueous alkanol or an aqueous acetone at a temperature of from ambient temperature to the refluxing temperature of the aqueous alkanol or aqueous acetone employed, to produce the desired 9,3″,4‴-tri-alkanoyl SF-837 $M_1$ substance of the formula (II) as defined in claim 1.

* * * * *